United States Patent
Chang

(10) Patent No.: US 7,049,086 B2
(45) Date of Patent: May 23, 2006

(54) HIGH-THROUGHPUT SCREENING ASSAY FOR CHOLESTEROL INHIBITORS AND INHIBITORS IDENTIFIED THEREBY

(75) Inventor: Ta-Yuan Chang, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 135 days.

(21) Appl. No.: 10/469,183

(22) PCT Filed: Feb. 25, 2002

(86) PCT No.: PCT/US02/05692

§ 371 (c)(1),
(2), (4) Date: Aug. 26, 2003

(87) PCT Pub. No.: WO02/068681

PCT Pub. Date: Sep. 6, 2002

(65) Prior Publication Data

US 2004/0115613 A1    Jun. 17, 2004

Related U.S. Application Data

(60) Provisional application No. 60/271,647, filed on Feb. 27, 2001.

(51) Int. Cl.
*C12Q 1/00*  (2006.01)
*C12Q 1/60*  (2006.01)

(52) U.S. Cl. .............................................. 435/11; 435/4
(58) Field of Classification Search .................... 435/4, 435/11
See application file for complete search history.

(56) References Cited

U.S. PATENT DOCUMENTS

| 4,939,134 A | * | 7/1990 | Javitt et al. | ................. 514/177 |
| 5,091,419 A | * | 2/1992 | Ito et al. | ..................... 514/596 |
| 5,494,791 A | * | 2/1996 | Cohen | ........................ 435/7.9 |

OTHER PUBLICATIONS

Millard et al., "Niemann-Pick Type C1 (NPC1) Overexpression Alters Cellular Cholesterol Homeostatis", J. Biol. Chem. 2000 275 (49):38445-38451.
Roff et al., "Type C Niemann-Pick Disease: Use of Hydrophobic Amines to Study Defective Cholesterol Transport", Dev. Neurosci. 1991 13:315-319.

* cited by examiner

*Primary Examiner*—Leon B. Lankford, Jr.
*Assistant Examiner*—Ruth A. Davis
(74) *Attorney, Agent, or Firm*—Licata & Tyrrell P.C.

(57) ABSTRACT

The present invention provides a high-throughput screening assay to identify test agents as cholesterol inhibitors via mutant NCP1 mammalian cells. Also provided are cholesterol inhibiting agents identified in accordance with this assay and methods for using such agents to inhibit cholesterol accumulation in cells.

6 Claims, 1 Drawing Sheet

HIGH-THROUGHPUT SCREENING ASSAY FOR CHOLESTEROL INHIBITORS AND INHIBITORS IDENTIFIED THEREBY

This applications claims the benefit of Provisional Application No. 60/271,647, filed Feb. 27, 2001.

INTRODUCTION

Work described herein was supported by funding from the National Institutes of Health (Grant No. HL 36709) and the United States Government may have certain rights in this invention.

FIELD OF THE INVENTION

The present invention relates to a high-throughput screening assay for identification of agents which inhibit or prevent the accumulation of cholesterol in cells. More specifically, this cell-based assay can be used to identify agents which block internalization of plasma membrane cholesterol from entering the cell interior. Agents identified in accordance with this method are expected to be useful in treatment of cardiovascular as well as neurodegenerative diseases associated with cholesterol accumulation.

BACKGROUND OF THE INVENTION

Genetic disorders have provided important model systems to identify factors and mechanisms involved in intracellular lipid metabolism and trafficking. For example, human fibroblast (Hf) cells from patients homozygous in familial hypercholesteremia have been used to elucidate the low density lipoprotein receptor pathway involved in regulation of intracellular cholesterol metabolism (Brown, M. S. and Goldstein, J. L. Science 1986 232:34–47). Niemann-Pick type C disease has also provided important insights into cholesterol metabolism. Niemann-Pick type C disease is an autosomal recessive, neurovisceral disorder that affects children who carry homozygous forms of the mutant NPC1 gene (Carstea et al. Science 1997 277:228–231) and causes death before adulthood. Hf cells from patients with Niemann-Pick type C disease have been found to accumulate LDL-derived cholesterol as unesterified cholesterol in an intracellular compartment (Pentchev et al. Proc. Natl Acad. Sci. USA 1985 82:8247–8251; Pentchev et al. FASEB J. 1987 1:40–45; and Liscum et al. J. Cell Biol. 1989 108:1625–1636).

The human NCP1 gene has been cloned, thus providing a better understanding of Niemann-Pick type C disease at the molecular level (Cartsea et al. Science (1997) Proc. Natl Acad. Sci. USA 1997 277:228–231). Final cloning work involved the identification of a 300 kb human genomic DNA containing the candidate NCP1 gene (Gu et al. Proc. Natl Acad. Sci. USA 1997 94:7378–7383). This unique DNA was identified by its ability to complement the defect of a previously isolated Chinese hamster ovary (CHO) cholesterol trafficking mutant, CT60 (Cadigan et al. J. Cell Biol. 110:295–308). The human NCP1 gene encodes an integral membrane protein with 1278 amino acids and contains the "sterol-sending domains" (Watari et al. J. Biol. Chem. 1999 274:2111861–21866) identified in several other integral membrane proteins that respond to endoplasmic reticulum (ER) cholesterol.

In mammalian cells, low density lipoprotein (LDL) binds to its receptor and internalizes and enters the endosomes/lysosomes for hydrolysis of the lipid cargo cholesteryl esters (Brown, M. S. and Goldstein, J. L. Science 1986 232: 34–47). Previously Niemann Pick type C (NPC) cells were believed to be defective in the movement of LDL-derived cholesterol from the hydrolytic organelle to the plasma membrane, thereby leading to cholesterol accumulation in the lysosomes (Liscum et al. J. Cell Biol. 1989 108:1625–1636; Neufeld et al. 1996 J. Cell Biol. 271: 21604–21613). Evidence at the microscopic level, however, illustrated cholesterol to accumulate in the late endosomes of NPC cells (Neufeld et al. J. Biol. Chem. 1999 274: 9627–9635; Kobayashi et al. Nat. Cell Biol. 1999 1:113–118) In additional studies, the movement of LDL-derived cholesterol from the lysosomes to the plasma membrane in NPC-like cells was shown not to be defective (Lange et al. J. Biol. Chem. 1998 J. Biol. Chem 273: 18915–18922). Using two independently isolated cholesterol-trafficking mutants defective in NPC1, namely CT60 and CT43, a NPC1 stable transfectant and their parental cells, 25RA CHO cells, Cruz et al. recently disclosed evidence that NPC1 is involved in post-plasma membrane cholesterol trafficking (Cruz et al. J. Biol. Chem. 2000 275(6):4013–4021). Specifically NPC1 was found to cycle cholesterol from an intracellular compartment to the plasma membrane or to the endoplasmic reticulum, but not prior to, newly hydrolyzed LDL-derived cholesterol appears in the plasma membrane (Cruz et al. J. Biol. Chem. 2000 275(6): 4013–4021).

SUMMARY OF THE INVENTION

An object of the present invention is to provide a high-throughput screening assay to identify test agents as cholesterol inhibitors. In the assay of the present invention, mutant NCP1 mammalian cells, preferably CHO CT43 or CHO CT60 cells, are exposed to a test agent. The ability of the test agent to increase sterol efflux in the media of the cells is evaluated, preferably via a pulse chase protocol. An increase in levels of sterol efflux in the media of the mutant NCP1 cells exposed to the test agent as compared to mutant NCP1 cells not exposed to the test agent is indicative of the test agent being a cholesterol inhibitor. Preferred cholesterol inhibitors of the present invention increase the sterol efflux level in the media of mutant mammalian NCP1 cells to the same level as observed in parenteral cells, preferably 25RA cells, not exposed to the test agent.

Another object of the present invention is to provide cholesterol inhibitors identified in accordance with this high-throughput screening assay. Cholesterol inhibitors identified in accordance with the assay of the present invention are expected to be useful in preventing endogenous cholesterol accumulation observed in cardiovascular diseases as well as neurodegenerative disorders such as atherosclerosis. Such agents are also useful in the treatment of Niemann Pick type C disease.

DETAILED DESCRIPTION OF THE INVENTION

Figure 1:
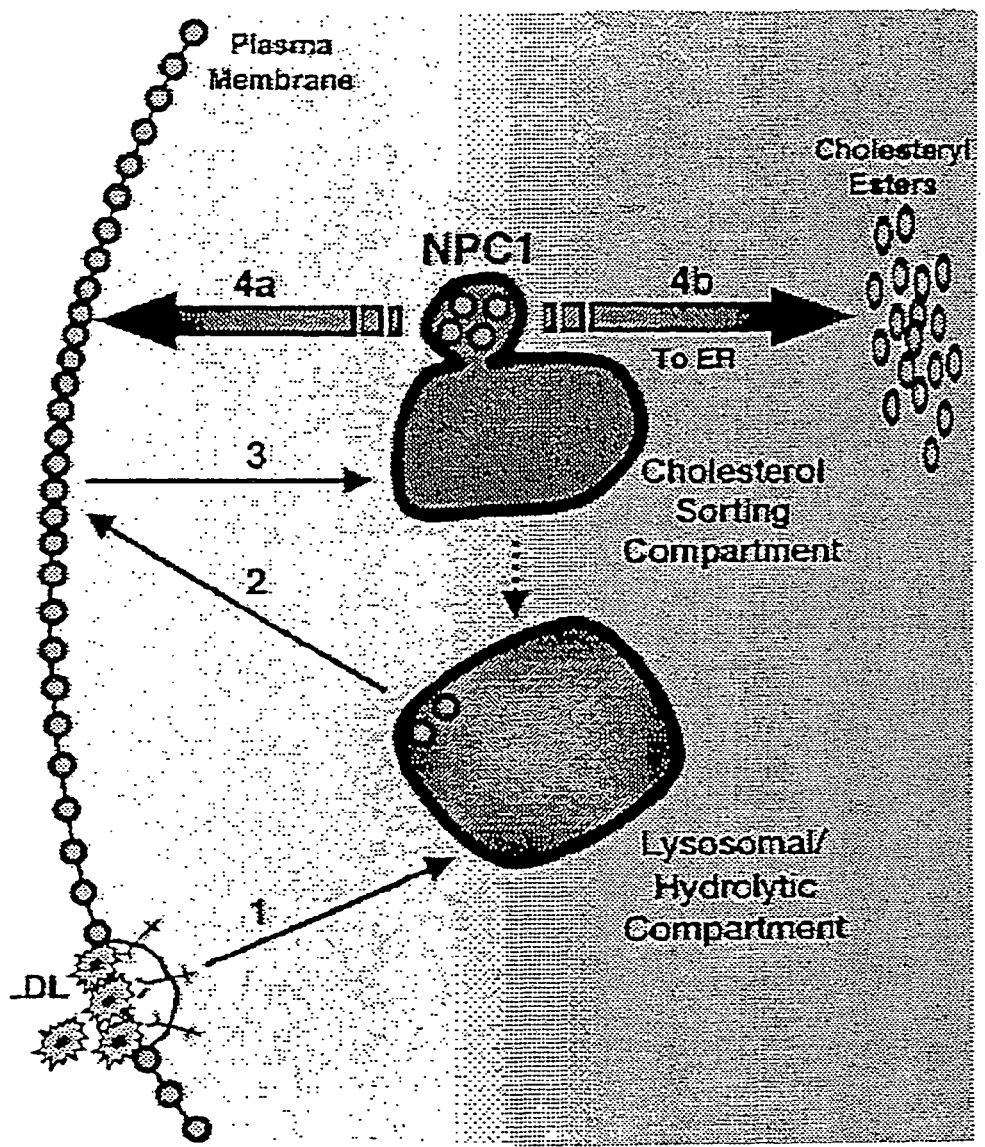
FIG. 1 provides a working model of the intracellular trafficking of LDL-derived cholesterol in mammalian cells. In step 1, LDL crosses the plasma membrane and enters the lysosomal/hydrolytic compartment. Initial movement of LDL cholesterol derived from the early hydrolytic degradative organelles to the plasma membrane (step 2) does not require NCP1. Upon reaching the plasma membrane, LDL-derived cholesterol is internalized into an intracellular compartment, designated the cholesterol sorting compartment (step 3). NCP1 is involved in the movement of cholesterol from this intracellular compartment back to the plasma membrane (step 4a) and to the endoreticulum for esterification (step 4b).

Lipoproteins are macromolecular complexes that carry hydrophobic plasma lipids, particularly cholesterol and triglyceride in the plasma. More than half of the coronary heart disease in the United States is attributable to abnormalities in the levels and metabolism of plasma lipids and lipoproteins. Premature coronary heart disease is sometimes related to mutations in the major genes involved in lipoprotein metabolism. However, elevated lipoprotein levels in most patients with coronary heart disease reflect the adverse impact of excess body weight and diets high in total and saturated fats. Elevated lipoprotein levels in the brain have also been associated with neurodegenerative disorders such as Alzheimer's disease.

Treatment of elevated LDL cholesterol is typically either focused at disease prevention or secondary treatment after complications have occurred. The rationale for primary prevention is based on a large body of evidence linking elevated levels of LDL cholesterol with an increase in coronary heart disease as well as clinical and experimental data demonstrating that reducing LDL cholesterol slows progression and may actually induce regression of coronary heart disease.

Three classes of lipid-lowering agents are presently recommended as first line therapy against hypercholesteremia. These include bile acid sequestrants or binding resins, niacin and 3-hydroxy-3-methyl glutaryl-coenzyme A (HMG-CoA) inhibitors. Recent cloning of the cDNA for human-specific acyl coenzyme A:cholesterol acyltransferase (ACAT) has also enabled research efforts focused on development of ACAT inhibitors for the therapeutic prevention and treatment of human hypercholesteremia and human atherosclerosis. However, there is a need for additional cholesterol inhibiting agents as well as screening assays for these agents.

The present invention provides a high-throughput screening assay for use in evaluating and identifying test agents with the ability to inhibit internalization of LDL-derived cholesterol into an intracellular compartment, designated the cholesterol sorting compartment (step 3 of FIG. 1). Agents with this ability will block cholesterol accumulation within cells and will increase sterol efflux. Accordingly, such agents are expected to be useful as cholesterol inhibitors in the treatment of diseases and disorders relating to over accumulation of cholesterol in cells.

The assay of the present invention is a cell-based assay which uses mammalian cells with a defective or mutant NCP1 gene, such as CHO CT43 or CT60 cells. CHO CT43 cells have been described and characterized in detail in references by Cruz et al. (J. Biol. Chem. 2000 275(6): 4013–4021) and Cruz and Chang (J. Biol. Chem. 2000 275(52) 41309–41316). CHO CT60 cells have been described by Cadigan et al. (J. Cell Biol. 1990 110:295–308) Culture conditions for growth of these cells are set forth in Example 2. In the screening assay of the present invention, the mutant NCP1 cells are exposed to a test agent. The ability of the test agent to increase sterol efflux, preferably via a pulse chase protocol, in the media of the cells is then evaluated. An increase in levels of sterol efflux in the media of mutant cells exposed to the test agent as compared to mutant cells not exposed to the test agent is indicative of the test agent being a cholesterol inhibitor. In a preferred embodiment of the present invention, the mutant cells comprise CHO CT43 or CT60 cells and levels of sterol efflux level in the media of these cells when exposed to a test agent are compared to sterol efflux levels of parenteral 25RA cells not exposed to the test agent. In this embodiment, test agents which increase the level of sterol efflux in the media close to the level in 25RA cells are expected to be potent cholesterol inhibitors.

It is preferred that the screening assay of the present invention be performed in a microtiter well format so that multiple test agents at various concentrations can be evaluated simultaneously. In this embodiment, mutant NPC1 cells are seeded into the wells of a microtiter plate. Sterol efflux in the media is preferably measured via a pulse chase protocol comprising detection of labeled cholesteryl linoleate-LDL. Examples of detectable labels include, but are not limited to, radiolabels, fluorophores and enzymes. In addition to mutant NCP1 cells exposed to various test agents, it is preferred that additional wells containing only mutant cells and only parenteral cells also be included as negative and positive controls for the assay. Wells containing only mutant cells provide a negative control as sterol efflux levels are expected to be low in these cells. These negative controls can be used to determine increases in sterol efflux levels of the mutant cells upon exposure to the test agents. Increase in sterol efflux levels upon exposure to the test agent as compared to the negative control is indicative of the test agent being a cholesterol inhibitors. Wells containing the parenteral cells provide a positive control of sterol efflux levels in normal cells. Test agents which increase sterol efflux levels to levels of the positive control are expected to be very effective cholesterol inhibitors.

In a preferred embodiment, the mutant cells used in the microtiter well format comprise CT43 cells or CT60 cells and are seeded at approximately $3-4 \times 10^4$ cells per well in medium A comprising Ham's F-12, 10% FBS, and 10 µg/ml gentamycin). Control cells comprising the parenteral 25RA cells are seeded at approximately $1 \times 10^4$ cells/well. In this embodiment, the medium is removed after one day, the cells are rinsed with phosphate buffered saline (PBS) and the medium is changed to Medium D comprising Ham's F12, 5% delipidated FBS, 10 mM Hepes, pH 7.4, 35 µM oleic acid, and 10 µg/ml gentamycin. The CT43 or CT60 cells are then incubated for an additional 36 hours. Prior to the pulse-chase experiment, cells are prechilled at 4° C. for 30 to 45 minutes. For the pulse, the cells are then incubated with [$^3$H]cholesteryl linoleate-labeled LDL (Approximately 30 µg LDL/ml medium; specific activity 30,000–50,000 cpm/µg protein, in 0.1 ml of medium D with sodium carbonate) at approximately 14° C. for about 4 hours. Cells are then washed and various test agents and/or various concentrations of a single test agent are then added to the wells and the plates are incubated at approximately 4° C. for about 1 hour. In a preferred embodiment the test agents are dissolved at high concentration in dimethyl sulfoxide (DMSO) so that the final concentration of DMSO in the assay is less than or equal to 1%. Typical concentrations of test agent examined range from 1 to 100 µM. Following this incubation, the cells are chased with an aliquot of medium D at 37° C. for various times ranging between 1 to 4 hours. The cells are then subjected to 2% 2-hydroxypropyl D-β-cyclodextrin (CD) in medium D at 37° C. for 30 minutes. The CD-containing media and the cells can then be processed for radioactive counting via direct counting as set forth in Example 3 or thin layer chromatography as set forth in Example 4. Using this microtiter well format of the assay of the present invention, CHO CT43 cells not exposed to any test agent were demonstrated to have significantly lower sterol efflux in their medium as compared to parenteral CHO 25RA cells.

Agents identified as cholesterol inhibitors in accordance with the method of the present invention can block the internalization of plasma membrane cholesterol from entering the cell interior thereby causing cholesterol to accumulate in the plasma membrane and promoting cholesterol efflux and stimulating reverse cholesterol transport in various body cells. These agents are expected to slow the development of atherosclerosis. Agents identified as inhibitors in accordance with the method of the present invention can also block the internalization of plasma membrane cholesterol in intestinal enterocytes, thereby preventing dietary cholesterol absorption. Such agents can also slow down the accumulation of amyloid beta-peptides in the brain, thereby slowing down the symptoms of Alzheimer's disease. Accordingly, test agents identified as cholesterol inhibitors in accordance with the assay of the present invention are expected to be useful in preventing and treating cardiovascular and neurodegenerative disease associated with over accumulation of cholesterol in cells. Such agents are also expected to be useful in the treatment of Niemann Pick type C disease.

The following nonlimiting examples are provided to further illustrate the present invention.

EXAMPLES

Example 1

Cell Lines

25RA cells are a Chinese Hamster Ovary (CHO) cell line resistant to the cytotoxicity of 25-hydroxycholesterol containing a gain of function mutation in the SREBP cleavage-activating protein (SCAP). CT43 cells are derived from 25RA cells and are defective in NPC1.

Example 2

Cell Culture

CHO cells were seeded in medium A (Ham's F-12, 10% fetal bovine serum, and 10 µg/ml gentamicin) as monolayers at 37° C. with 5% $CO_2$ on day 1. On day 2, cells were incubated with medium D at 37° C. When used at 37° C., medium D refers to Ham's F-12 with 5% delipidated fetal bovine serum, 35 µM oleic acid, 1.5 mM $CaCl_2$, and 10 µg/ml gentamicin; when used at 14° C., medium D refers to the same medium without sodium bicarbonate and supplemented with 20 mM HEPES, pH 7. Al experiments were conducted on day 4, when the cells were 80–90% confluent.

Example 3

Direct Counting

The cyclodextrin (CD)-containing media were transferred from the wells into scintillation vials and 3 ml of ECONOSCINT (National Diagnostics) was added to each vial and counted for radioactivity. As soon as the CD-containing medium was removed, cells were washed with PBS twice, and 100 µl of 0.2 M of freshly prepared NaOH was added to each well to lyse the cells. After 30–45 minutes at room temperature, cell extracts were transferred into scintillation vials and 6.5 µl of 3M HCl and 6.2 µl of 1 M $KH_2PO_4$, pH 7.0, were added to neutralize the cells. ECONOSCINT (3 ml) was then added to each vial, and processed for scintillation counting.

Example 4

Counting After Lipid Extraction and TLC Separation

The CD-containing medium was removed from the well and placed into a 13×100 mm glass tube. After washing twice with PBS, cells were lysed with 100 µl of 0.2M NaOH, transferred into the glass tube, and neutralized with HCl/$KH_2PO_4$ by the procedure described in Example 3. Chloroform/methanol (2:1; 3 ml) was added to each sample and vortexed well. $H_2O$ (12 ml) was then added and the sample was vigorously vortexed. The samples were centrifuged at 1,000 g for 10 minutes, and the upper phase (aqueous phase) was removed. The remaining organic phase was dried under $N_2$, and 100 µl of hexane (containing 1 mg/ml cold cholesterol) was added to each sample with vigorous vortex. The samples were spotted on Silica Gel TLC plate. The lipids were separated using the 90:10:1 of petroleum ether/ether/acetic acid solvent system. The plate was subjected to $I_2$ staining to visualize the lipids, the band corresponding to cholesterol was scraped into the scintillation vial, solubilized with 3 ml of BETAFLUOR (from National Diagnostics), and counted for radioactivity. % Efflux was calculated as the amount of [$^3$H] cholesterol in medium divided by the sum of [$^3$H] cholesterol in medium and in cell extract.

What is claimed is:

1. A high-throughput screening assay for identification of cholesterol inhibitors comprising exposing mutant NPC1 mammalian cells to a test agent, measuring a sterol efflux level in media of the mutant NPC1 mammalian cells exposed to the test agent, and comparing the measured level to a sterol efflux level in mutant NPC1 cells not exposed to the test agent, wherein an increase in the measured sterol efflux level in the mutant NPC1 cells exposed to the test agent as compared to the level in mutant NPC1 cells not exposed to the test agent is indicative of the test agent being a cholesterol inhibitor.

2. The method of claim 1 wherein the mutant NPC1 cells comprise CHO CT43 or CT60 cells.

3. The method of claim 1 wherein sterol efflux levels are measured via a pulse chase protocol.

4. A high-throughput screening assay for identification of cholesterol inhibitors comprising exposing mutant NPC1 mammalian cells to a test agent, measuring a sterol efflux level in media of the mutant NPC1 mammalian cells exposed to the test agent, and comparing the measured level to a sterol efflux level in parenteral cells not exposed to the test agent, wherein a measured sterol efflux level in the mutant NPC1 cells exposed to the test agent equal to the sterol efflux level in parenteral cells test agent is indicative of the test agent being a cholesterol inhibitor.

5. The method of claim 1 wherein the mutant NPC1 cells comprise CHO CT43 or CT60 cells and the parenteral cells comprise CHO 25RA cells.

6. The method of claim 4 wherein sterol efflux levels are measured via a pulse chase protocol.

* * * * *